United States Patent
Bell

(10) Patent No.: US 7,326,573 B2
(45) Date of Patent: Feb. 5, 2008

(54) ASSAY PROCEDURES AND APPARATUS

(75) Inventor: Michael L. Bell, Fullerton, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 633 days.

(21) Appl. No.: 10/340,278

(22) Filed: Jan. 10, 2003

(65) Prior Publication Data

US 2004/0137635 A1    Jul. 15, 2004

(51) Int. Cl.
*G01N 33/48*    (2006.01)
*G01N 33/00*    (2006.01)
*G01N 21/76*    (2006.01)

(52) U.S. Cl. .................. 436/63; 435/7.92; 436/63; 436/172

(58) Field of Classification Search .................. 436/63, 436/172; 435/7.92
See application file for complete search history.

(56) References Cited

U.S. PATENT DOCUMENTS

| | | | |
|---|---|---|---|
| 4,499,052 A | 2/1985 | Fulwyler .................. 422/52 |
| 4,665,020 A | 5/1987 | Saunders .................. 435/7 |
| 4,699,828 A | 10/1987 | Schwartz et al. ............. 436/8 |
| 5,028,545 A | 7/1991 | Soini ...................... 436/172 |
| 5,073,497 A | 12/1991 | Schwartz .................. 436/8 |
| 5,385,822 A | 1/1995 | Melnicoff et al. | |
| 5,646,001 A | 7/1997 | Terstappen et al. | |
| 5,674,698 A * | 10/1997 | Zarling et al. ............ 435/7.92 |
| 5,747,349 A | 5/1998 | Van den Engh et al. .... 436/172 |
| 5,786,219 A | 7/1998 | Zhang et al. | |
| 5,962,238 A * | 10/1999 | Sizto et al. ............... 435/7.24 |
| 5,981,180 A | 11/1999 | Chandler et al. ............. 435/6 |
| 5,985,153 A | 11/1999 | Dolan et al. | |
| 6,023,540 A | 2/2000 | Walt et al. .................. 385/12 |
| 6,159,748 A | 12/2000 | Hechinger ................. 436/51 |
| 6,165,796 A | 12/2000 | Bell ........................ 436/74 |
| 6,225,046 B1 | 5/2001 | Vesey et al. | |
| 6,280,618 B2 | 8/2001 | Watkins et al. | |
| 2002/0115116 A1 | 8/2002 | Song et al. | |

FOREIGN PATENT DOCUMENTS

| | | |
|---|---|---|
| EP | 0121262 A2 | 10/1984 |
| EP | 126450 | 11/1984 |
| EP | 0219309 A1 | 4/1987 |
| WO | WO 00/67894 A2 | 11/2000 |
| WO | WO 01/13120 | 2/2001 |

OTHER PUBLICATIONS

U.S. Appl. No. 09/991,001, filed Nov. 14, 2001.

(Continued)

*Primary Examiner*—Jill Warden
*Assistant Examiner*—Lore Ramillano
(74) *Attorney, Agent, or Firm*—Marc Karish; Sheldon Mak Rose & Anderson

(57) ABSTRACT

In cytometry and like procedures, particles containing signal dyes are exposed to a laser, and the resulting fluorescence is assessed in two different wavelength bands. When the particle is a single-assay particle, or when the particle carries only a single dye, the fluorescences in the different wavelength bands are combined in order to assess the concentration of the signal dye.

10 Claims, 2 Drawing Sheets

OTHER PUBLICATIONS

Lutz, E.S.M. et al., "Implementation of affinity solid-phases in continuous-flow biochemical detection," Journal of Chromatography, (1997), pp. 169-178, vol. 776, No 2.

Nanthakumar, A. et al., "Solid-Phase Oligonucleotide Synthesis and Flow Cytometric Analysis with Microspheres Encoded with Covalently Attached Fluorophores," Bioconjugate Chem. (2000) pp. 282-288, vol. 11.

* cited by examiner

ASSAY PROCEDURES AND APPARATUS

BACKGROUND OF THE INVENTION

1. Field of the Invention

This invention relates to assay apparatus and procedures.

2. Introduction

In bead-based flow cytometry and similar assay procedures, the sample to be assayed is contacted with a multitude of particles. All the particles are coded for recognition purposes and contain analyte-interaction sites which interact selectively with one or more of the analytes in the sample. The particles and the sample are contacted for a time and under conditions such that the desired interaction takes place. The particles fall into different categories. In each category, all the particles (a) have the same coding characteristic, and (b) contain the same analyte-interaction sites.

The coding characteristic and the analyte-interaction sites in each category are different from those in all the other categories.

Before, during or after the contacting of the particles and the sample, the analytes and/or the sites which have interacted with the analytes are labeled with a signal label. The interaction between the analyte interaction sites can be of any kind, for example the formation of a covalent, coordinate or ionic bond, hybridisation of nucleotides, or enzymatic action. The term "analyte-bearing site" is used herein to denote any analyte interaction site which has interacted with an analyte, even if the analyte itself is not present at the site after the interaction. In some assays, an alternative to labeling the analytes and/or the analyte-bearing sites is so-called competitive assay. In a competitive assay, before, during or after the sample has been contacted with the reagent, analogs of the analytes are added to the sample, or to the reagent, or to the mixture of the sample and the reagent; and before, during or after such addition, the analogs and/or the analyte-bearing sites, are labeled with signal labels. In this specification, when reference is made to a signal label "associated" with an analyte or with an analyte-bearing site, the signal label can be one which identifies, in any way, interaction between an analyte and an analyte-interaction site, for example a signal label which is (a) attached to an analyte or to an analyte-bearing site, or (b) attached to an analyte analog, or to an analyte-bearing site, as part of a competitive assay.

A representative sample of the particles is then examined, one particle at a time, in a cytometer (or like instrument) which recognizes the coding characteristic and the signal labels. On each particle, the coding characteristic identifies the analyte-interaction site, and the signal label(s) identifies (and usually quantifies) the analyte(s).

The coding characteristic on the particles is often provided by securing known amounts of one or both of two different fluorochromes to each particle. The cytometer (or other instrument) identifies the categories of particle by assessing the relative and/or absolute amounts of the fluorescence derived from the fluorochromes when they are exposed to a laser. Different categories of particles can alternatively or additionally be distinguished by other coding characteristics, for example by size, density, radioactivity, color, electrical charge, or magnetic properties.

The particles can be of different types, which are referred to herein as single-assay particles and multi-assay particles.

Single-assay particles contain analyte-interaction sites which can interact with (a) only one analyte, or (b) two or more analytes which do not need to be separately assayed on that particle. Associated assay particles are a particular class of single-assay particles. They contain analyte-interaction sites which can interact with all the analytes in a group of two or more analytes, and belong to two or more different categories, the number of categories being at least equal to the number of analytes in the group. The associated assay particles in each category contain analyte-interaction sites which are different from the analyte-interaction sites in each of the other categories. However, all the different analyte-interaction sites can interact with each analyte in the group of analytes, and the affinity of each of the analytes in the group for each of the analyte-interaction sites is known. The results of examining the associated assay particles in the different categories can, therefore, be analyzed together to assay each analyte.

Multi-assay particles contain analyte-interaction sites which interact with two or more analytes which must be separately assayed on each particle. Such particles require different signal labels to be associated with each of the different analytes. Multi-assay particles are usually dual-assay particles, i.e. they interact with only two different analytes. One important use of dual-assay particles is to assay two different types of rubella antibody, which may for example be labeled by different signal dyes before, during or after they interact with the particles.

Cytometers are often set up so that they can carry out both assays in which only single-assay particles are used and assays in which both single-assay and dual-assay particles are used.

It is generally convenient for dual-assay particles to use a pair of signal dyes which will fluoresce when exposed to the same laser, and for single-assay particles being assayed at the same time to use one of that pair of signal dyes, or another signal dye which will fluoresce when exposed to the same laser. However, such signal dyes generally fluoresce in spectra which have different peaks but which overlap substantially. This makes it difficult to assess separately the fluorescence produced by the respective signal dyes, especially when one of the signal dyes is present in much higher concentration than the other. The conventional practice is to split the fluorescence from the particle (whether it is a single-assay or dual-assay particle) into two relatively narrow and widely separated spectral bands. The fluorescence in one of the bands is derived principally from one of the signal dyes and the fluorescence in the other band is derived principally from the other signal dye. The accompanying FIG. 1 shows typical fluorescence spectra for a pair of signal dyes and the wavelength bands in which their fluorescence is conventionally assessed. As a result, only a fraction of the spectrum of each signal dye is assessed, and the sensitivity of the system is low. If the spectral bands are widened, the sensitivity of the system is increased, but the signal levels must be deconvolved mathematically to assign reliable values to each signal dye. This deconvolution requires knowledge of the spectra of the two signal dyes, and since these spectra may change in an unknown way in response to the microenvironment as the particle is being examined, errors may be introduced.

For disclosure of bead-based cytometry and similar assay procedures, reference may be made for example to U.S. Pat. Nos. 4,499,052 (Fulwyler), 4,665,020 (Saunders), 4,699,828 (Schwartz et al), 5,028,545 (Soini), 5,073,497 (Schwartz), 5,747,349 (van den Engh et al), 5,981,180 (Chandler et al.), 6,023,540 (Walt et al), 6,159,748 (Hechinger) and 6,165,796 (Bell), European Patent No. 126,450, WO 01/13120, and copending, commonly assigned, U.S. application Ser. No.

09/991,001, filed Nov. 14, 2001, the entire disclosures of which are incorporated by reference herein for all purposes.

SUMMARY OF THE INVENTION

I have realized, in accordance with the present invention, that improved results can be obtained by making the assessment of the fluorescence derived from a signal dye or dyes dependent on (1) the type of particle from which the fluorescence is derived, in particular whether it is a single-assay or multi-assay particle, or (2) the fluorescence itself, in particular whether the fluorescence is derived from a single signal dye or from more than one signal dye.

In a first aspect, this invention provides, in a method of examining a mixture of single-assay and dual-assay particles, the dual-assay particles having associated therewith one or both of a first fluorochromic signal dye and a second fluorochromic signal dye, and the single-assay particles having associated therewith a third fluorochromic signal dye which is the same as the first or the second signal dye or is different therefrom; the method comprising
  (A) exposing the particles, one at a time, to a laser which causes fluorescence of any fluorochromic signal dye associated with the particle; and
  (B) assessing separately (i) the fluorescence in a first wavelength band and (ii) the fluorescence in a second wavelength band;

the improvement which comprises, when the particle is a single-assay particle, or when the fluorescence is derived from a single signal dye, combining the fluorescence assessed in the first wavelength band with the fluorescence assessed in the second wavelength band.

In this specification, the term "combining" (and grammatical variations thereof) two or more fluorescences is used to denote any operation which results in a quantity which reflects the values of the two or more fluorescences which are combined. In some embodiments, the fluorescences are simply added to each other. However, the invention includes, for example, multiplying the values together, or subtracting one value from another. The combining can be effected on values obtained from each particle individually and/or on values obtained from some or all of particles in a particular category.

In one embodiment, each of the fluorescence values is multiplied by a weight, thus providing a weighted value, and the weighted values are then added to form a weighted sum, or are otherwise combined. The use of weighted sums is of particular value when the fluorescence values contain different relative amounts of noise. In such case, it is advantageous to use weights that are inversely related to the relative magnitude of the noise components of each fluorescence value. This reduces the effect of particularly noisy values on the combination. It is not unusual for fluorescence values to have different relative amounts of noise in different wavelength bands as fluorescence detectors (typically photomultiplier tubes or photodiodes) have different sensitivity in different wavelength bands. Dyes also produce different amounts of fluorescent light in different wavelength bands. Fluorescence detectors and subsequent signal processing circuitry are commonly adjusted to boost signals from normally received levels of fluorescent light to a common operating region. This means that wavelength bands where there is less fluorescent light or where the response of the fluorescence detector is relatively low, higher gain is typically applied. This gain amplifies the fluorescence value, but it also amplifies any noise that may be present. Reducing the weights of fluorescence values from such wavelength bands improves the signal to noise ratio of the resultant combination.

In a second aspect, this invention provides apparatus for examining a plurality of particles which are passed, one at a time, through the apparatus, each of the particles
  (i) having a coding characteristic,
  (ii) containing analyte-interaction sites and/or corresponding analyte-bearing sites and have associated therewith one or more fluorochromic signal dyes, and
  (iii) belonging to one only of a plurality of defined categories, each of the particles in each defined category
    (a) having the same coding characteristic, and
    (b) containing the same analyte-interaction sites and/or corresponding analyte-bearing sites;

the combination of the coding characteristic and the analyte-interaction sites and/or corresponding analyte-bearing sites on the particles in each category being different from the combination of the coding characteristic and the analyte-interaction sites and/or corresponding analyte-bearing sites on the particles in other categories;

the apparatus comprising
  (1) a coding determination system for determining the coding characteristic of each particle as it is passed through the apparatus;
  (2) a laser to which each particle is exposed as it is passed through the apparatus and which causes fluorescence of any fluorochromic signal dye associated with analyte-bearing sites on the particle; and
  (3) a fluorescence assessment system which comprises
    (i) a first detection channel for assessing fluorescence caused by the laser and falling within a first wavelength band,
    (ii) a second detection channel for assessing fluorescence caused by the laser and falling within a second wavelength band,
    (iii) a recording means which
      (A) when the coding determination system determines that the particle has a coding characteristic associated with a dual-assay particle, or when the detection channels detect fluorescence from two signal dyes, records separately the fluorescence assessed by the first detection channel and the fluorescence assessed by the second detection channel, and
      (B) when the coding determination system determines that the particle has a coding characteristic associated with a single-assay particle, or when the detection channels detect fluorescence from only a single signal dye, combines the fluorescence assessed by the first detection channel and the fluorescence assessed by the second detection channel.

In a third aspect, this invention provides a method of examining a composition which comprises a plurality of particles as defined in the second aspect of the invention, the method comprising examining, one at a time, each particle of a representative sample of the particles, the examination comprising
  (A) determining the coding characteristic of the particle;
  (B) subjecting the particle to radiation from a laser which causes fluorescence of any fluorochromic signal dye associated with analyte-bearing sites on the particle;
  (C) assessing the fluorescence caused by the laser and falling within a first wavelength band;

(D) assessing the fluorescence caused by the laser and falling within a second wavelength band; and (E) when step (A) determines that the particle is a single-assay particle, combining the fluorescence in the first wavelength band and the fluorescence in the second wavelength band, or when step (A) determines that the particle is a dual-assay particle, recording separately the fluorescence in the first wavelength band and the fluorescence in the second wavelength band.

In a fourth aspect, this invention provides a cytometer which is suitable for carrying out the method of the third aspect of the invention and which comprises a computer programmed so that (a) if a particle being examined by the cytometer is a dual-assay particle having associated therewith first and/or second fluorochromic signal labels, the cytometer assesses separately (i) fluorescence generated by the first and/or second signal labels in a first wavelength band, and (ii) fluorescence generated by the first and/or second signal labels in a second wavelength band; and (b) if a particle being examined by the cytometer is a single-assay particle having associated therewith a third fluorochromic signal label, the third signal label being the same as one of the first and second signal labels or different therefrom, the cytometer combines (i) fluorescence generated by the third signal label in the first wavelength band, and (ii) fluorescence generated by the third signal label in the second wavelength band.

In a fifth aspect, this invention provides a method of examining a composition which comprises a plurality of particles as defined in the second aspect of the invention, the method comprising examining, one at a time, each particle of a representative sample of the particles, the examination comprising (A) determining the coding characteristic of the particle;

(B) subjecting the particle to radiation from a laser which causes fluorescence of any fluorochromic signal dye associated with analyte-bearing sites on the particle;

(C) assessing the fluorescence caused by the laser and falling within a first wavelength band;

(D) assessing the fluorescence caused by the laser and falling within a second wavelength band; and (E) when the fluorescence assessed in steps (C) and (D) results from only a single signal dye, combining the fluorescence in the first wavelength band and the fluorescence in the second wavelength band, or when the fluorescence assessed in steps (C) and (D) results from two or more signal dyes, recording separately the fluorescence in the first wavelength band and the fluorescence in the second wavelength band.

In a sixth aspect, this invention provides a cytometer which is suitable for carrying out the method of the fifth aspect of the invention and which comprises a computer programmed so that (a) if a particle being examined by the cytometer has associated therewith first and second fluorochromic signal labels, the cytometer assesses separately (i) fluorescence generated by the first and/or second signal labels in a first wavelength band, and (ii) fluorescence generated by the first and/or second signal labels in a second wavelength band; and (b) if a particle being examined by the cytometer has associated therewith a single fluorochromic signal label, the cytometer combines (i) fluorescence generated by the signal label in the first frequency band, and (ii) fluorescence generated by the signal label in the second frequency band.

In a seventh aspect, this invention provides software which can be installed on a computer controlling a cytometer so that the cytometer will carry out the method of the third or the fifth aspect of the invention.

BRIEF DESCRIPTION OF THE DRAWINGS

The invention is illustrated in accompanying drawings, in which.

DETAILED DESCRIPTION OF THE INVENTION

In the Summary of the Invention above and in the Detailed Description of the Invention below, and in the accompanying drawings, reference is made to particular features (including method steps) of the invention. It is to be understood that the disclosure of the invention in this specification includes all appropriate combinations of such particular features. For example, where a particular feature is disclosed in the context of a particular aspect or embodiment of the invention, that feature can also be used, to the extent appropriate, in combination with and/or in the context of other particular aspects and embodiments of the invention, and in the invention generally.

In describing and claiming the invention below, the following definitions (in addition to those already given) are used. The term "comprises" (and grammatical variations thereof) in relation to methods, materials, things etc. is used herein to mean that the methods, materials, things etc. can optionally include, in addition to the steps, features, components, etc. explicitly specified after the term "comprises" (and grammatical variations thereof), other steps, features, ingredients, etc. Where reference is made herein to a method comprising two or more steps, the steps can be carried out in any order, or simultaneously, except where the context excludes that possibility. The term "at least" followed by a number is used herein to denote the start of a range beginning with that number (which may be a range having an upper limit or no upper limit, depending on the variable being defined). For example "at least 3" means 3 or more than 3. The term "at most" followed by a number is used herein to denote the end of a range ending with that number (which may be a range having 1 or 0 as its lower limit, or a range having no lower limit, depending upon the variable being defined). For example, "at most 4" means 4 or less than 4. When, in this specification, a range is given as "(a first number) to (a second number)" or "(a first number)—(a second number)", this means a range whose lower limit is the first number and whose upper limit is the second number.

Figure 1:
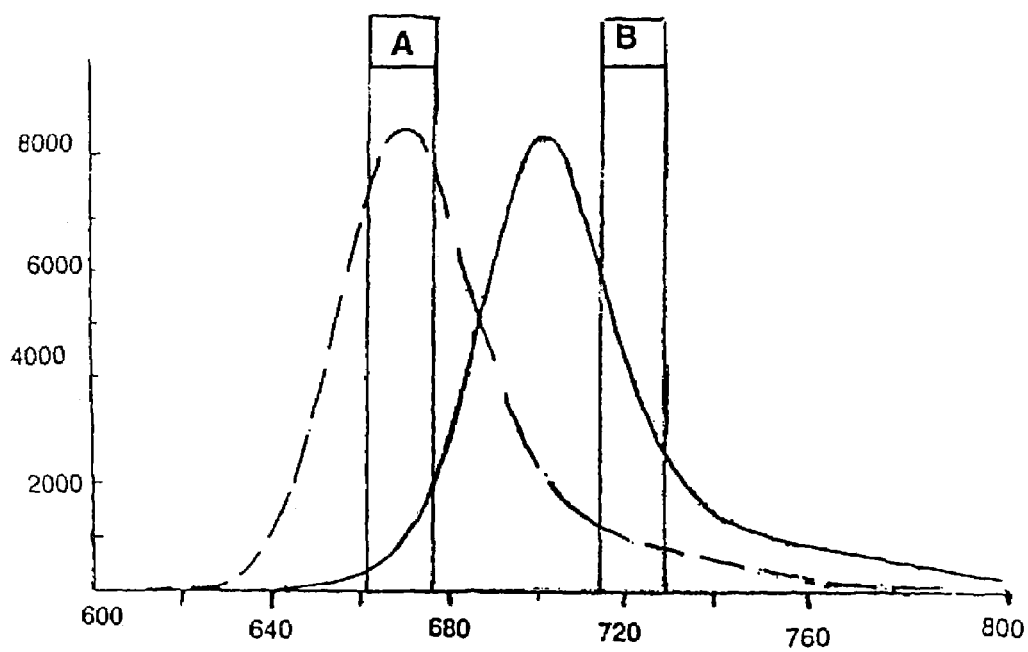
FIG. 1 is a graph showing typical fluorescence spectra for two signal dyes and conventional wavelength bands for assessing such fluorescence.

As noted above, it is conventional to use first and second relatively narrow and widely separated wavelength bands for detecting fluorescence derived from different signal labels, as illustrated for example in FIG. 1. The present invention can make use of such conventional wavelength bands, and under those circumstances, the changes required to implement the present invention may involve no more than re-programming a computer controlling a cytometer so that the fluorescences in the two wavelength bands, instead of being invariably recorded separately, are combined when the particle is a single-assay particle or when the particle contains only a single signal dye.

Preferably, however, the invention makes use of broader first and second wavelength bands, and/or makes use of a third wavelength band between the first and second bands, the fluorescence in the third wavelength band being combined with the fluorescences to in the first and second bands when the particle is a single-assay particle or when the particle contains only a single signal dye.

Figure 2:
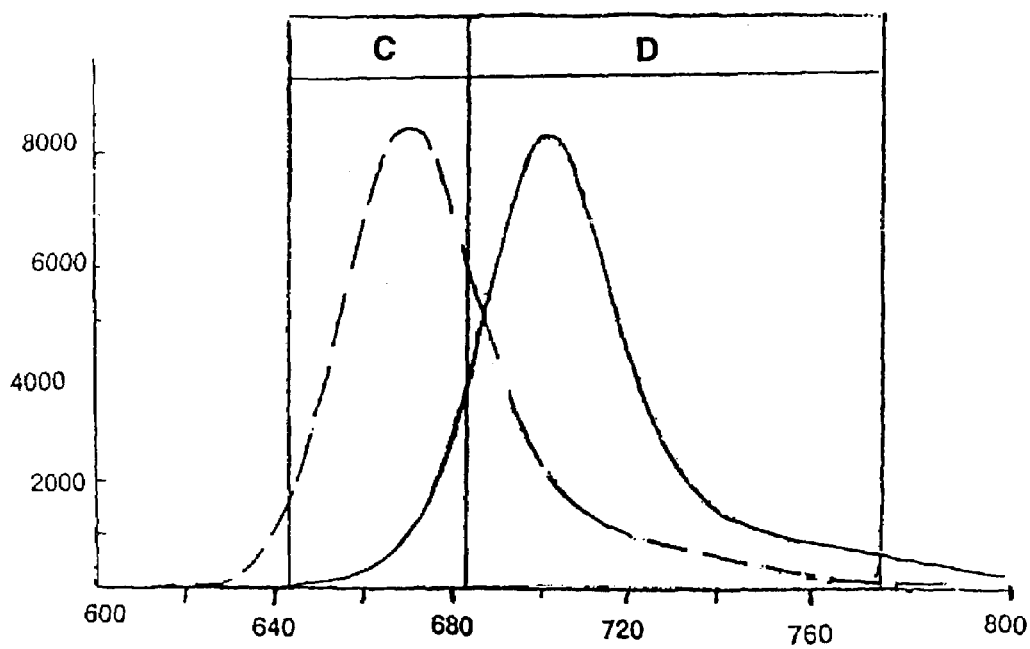
FIG. 2 is a graph showing the same fluorescence spectra as FIG. 1 and a preferred selection of wavelength bands for assessing such fluorescence in accordance with the present invention.
Figure 3:
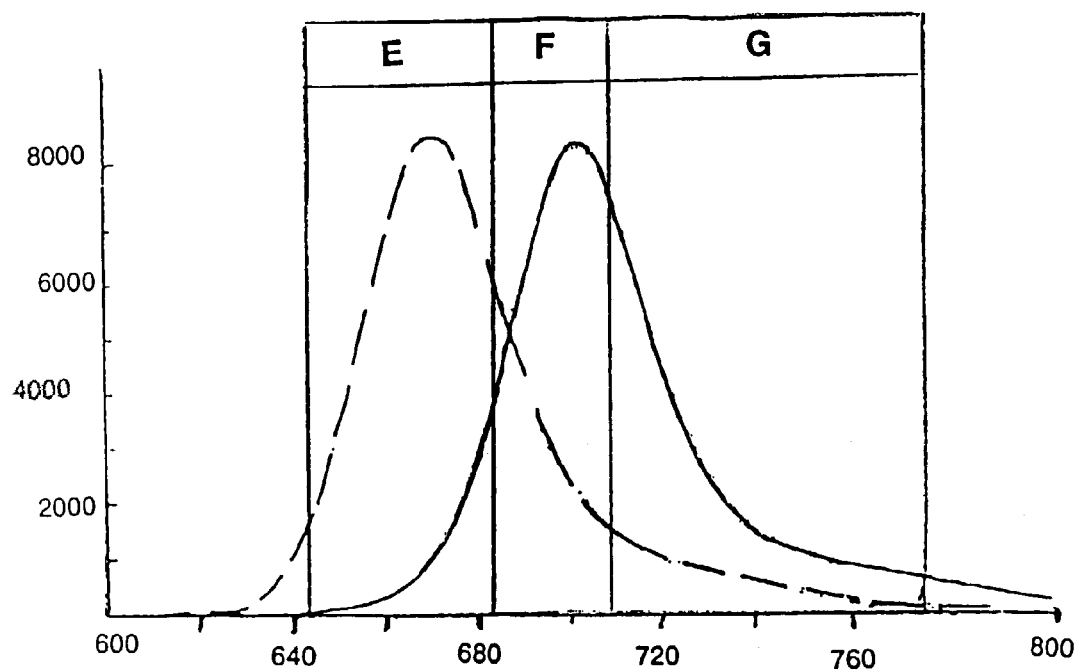
FIGS. 3 and 4 are graphs showing the same fluorescence spectra as FIG. 1 and alternative selections of first, second and third wavelength bands for assessing such fluorescence in accordance with the present invention.

In one embodiment, as illustrated in FIG. 2, the upper limit of first wavelength band is the same as the lower limit of second wavelength band. This can be accomplished by using dichroic beamsplitters. Dichroic beamsplitters are frequently employed in cytometers in conjunction with bandpass filters which are placed between the beamsplitters and the fluorescence detectors and which further narrow the wavelength bands produced by the beamsplitters. This invention makes it possible to remove at least some of these bandpass filters. In another embodiment of the invention, the first and second wavelength bands are separated by an intermediate wavelength band. The width of the intermediate wavelength band is preferably less than 3 times, particularly less than 2 times, especially less than 1 time, the sum of the widths of the first and second wavelength bands. The first wavelength band may contain the peak of the spectrum of the fluorescence derived from the first signal dye and/or the second wavelength band may contain the peak of the spectrum of the fluorescence derived from the second signal dye. When the fluorescence is assessed in a third wavelength band between the first and second wavelength bands, the third wavelength band can be the whole of the intermediate wavelength band between the first and second wavelength bands, as illustrated in FIG. 3, or only part of that intermediate wavelength band.

An advantage of the present invention is that it increases the sensitivity of the system. This makes it possible to detect analytes at lower concentrations and/or to reduce the incubation time (i.e. the time for which the particles are in contact with the solution to be analyzed before the particles are examined). The invention is particularly useful, for example, when (a) dual-assay particles are used in combination with single-assay particles which interact with one or more analytes which are likely to be present only in small concentrations, for example when the analyte is thyroid stimulating hormone (TSH), and/or (b) when the analytes that interact with a dual-assay particle are such that it is not necessary to know (or at least not necessary to know with great precision) the concentration of the analytes (as for example when detecting the two different types of rubella antibody).

Figure 4:
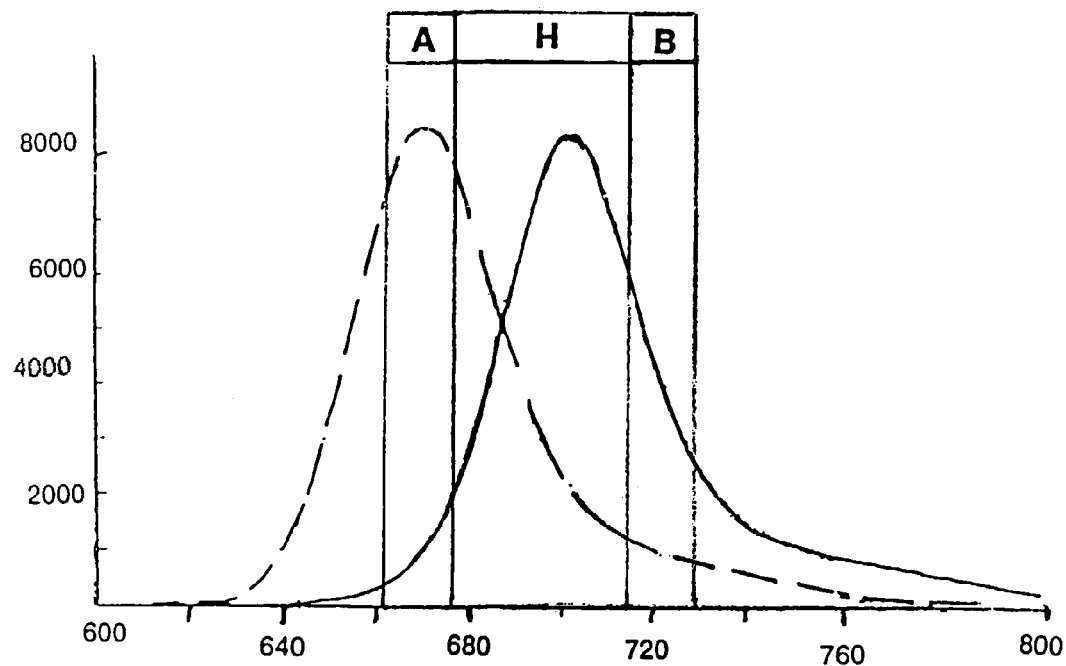

Referring now to the drawings, the fluorescence spectra shown in the Figures are the spectra of two cyanine dyes, Cy5 and dibenzoCy5, one of the spectra being shown as a dashed line. FIG. 1 shows narrow wavelength bands A and B in which the fluorescence from the two dyes is conventionally assessed in the prior art. FIG. 2 shows two broader wavelength bands C and D in which the fluorescence is assessed in accordance with the present invention. FIG. 3 shows three broader wavelength bands E, F and G in which the fluorescence is assessed in accordance with the present invention. FIG. 4 shows three wavelength bands A, B and H, wavelength bands A and B of being the same as in FIG. 1, in which the fluorescence is assessed in accordance with the present invention. It is apparent from the Figures that the amounts of fluorescence assessed in the present invention are substantially greater than the amounts assessed in the prior art procedure. The improvements in signal to noise is in general less, because the individual wavelength band measurements contribute more noise than if a single measurement were made over the combined wavelength band.

What is claimed is:

1. A method of examining a composition which comprises a plurality of particles, each of the particles
  (i) having a coding characteristic,
  (ii) containing analyte-interaction sites and/or corresponding analyte-bearing sites which are the same as said analyte-interaction sites except that they have interacted with one or more analytes and have associated therewith one or more fluorochromic signal dyes, and
  (iii) belonging to one only of a plurality of defined categories, each of the particles in each defined category
    (a) having the same coding characteristic, and
    (b) containing the same analyte-interaction sites and/or corresponding analyte-bearing sites;
the combination of the coding characteristic and the analyte-interaction sites and/or corresponding analyte-bearing sites on the particles in each category being different from the combination of the coding characteristic and the analyte-interaction sites and/or corresponding analyte-bearing sites on the particles in other categories;
  the method comprising examining, one at a time, each particle of a representative sample of the particles, the examination comprising:
  (A) determining the coding characteristic of the particle, including whether the particle is a single-assay particle or a dual-assay particle;
  (B) subjecting the particle to radiation from a laser which causes fluorescence of any fluorochromic signal dye associated with analyte-bearing sites on the particle;
  (C) assessing the fluorescence caused by the laser and falling within a first wavelength band;
  (D) assessing the fluorescence caused by the laser and falling within a second wavelength band; and
  (E) when step (A) determines that the particle is a single-assay particle, combining the fluorescence in the first wavelength band and the fluorescence in the second wavelength band, and
  when step (A) determines that the particle is a dual-assay particle, recording separately the fluorescence in the first wavelength band and the fluorescence in the second wavelength band.

2. A method according to claim 1 wherein
  (A) the plurality of particles includes
  (i) dual-assay particles containing analyte-bearing sites which
    (a) have interacted with a first analyte and have associated therewith a first fluorochromic signal dye, and/or (b) have interacted with a second analyte and have associated therewith a second fluorochromic signal dye; and (ii) single-assay particles containing analyte-bearing sites which have interacted with an analyte and have associated therewith a fluorochromic signal dye which is the same as the first or the second signal dye or is different therefrom;

(B) the laser (i) causes the first fluorochromic signal dye, if present, to fluoresce in a first spectrum, (ii) causes the second fluorochromic signal dye, if present, to fluoresce in a second spectrum which is different from but overlaps the first spectrum, and (iii) causes the fluorochromic signal dye or dyes associated with the single-assay particles, if present, to fluoresce in a spectrum which includes at least one of the first wavelength band and the second wavelength band.

3. A method according to claim 2 wherein the fluorescence from the first signal dye has a peak at a first peak frequency; the fluorescence from the second signal dye has a peak at a second peak frequency; the first wavelength band includes the first peak frequency; and the second wavelength band includes the second peak frequency.

4. A method according to claim 2 wherein the first and second wavelength bands are separated by an intermediate wavelength band whose width is 0 to 1 times the sum of the widths of the first and second wavelength bands.

5. A method according to claim 4 wherein the first wavelength band has an upper limit and the second wavelength band has a lower limit which is the same as the upper limit of the first wavelength band.

6. A method according to claim 2 which includes assessing the fluorescence in an intermediate wavelength band between the first and second wavelength bands, and, when step (A) determines that the particle is a single-assay particle, combining the fluorescences in the first, second and intermediate wavelength bands.

7. A method according to claim 2 wherein the single assay particles in one category interact with thyroid stimulating hormone.

8. A method of examining a composition which comprises a plurality of particles, each of the particles (i) having a coding characteristic, (ii) containing analyte-interaction sites and/or corresponding analyte-bearing sites which are the same as said analyte-interaction sites except that they have interacted with one or more analytes and have associated therewith one or more fluorochromic signal dyes, and (iii) belonging to one only of a plurality of defined categories, each of the particles in each defined category (a) having the same coding characteristic, and (b) containing the same analyte-interaction sites and/or corresponding analyte-bearing sites;

the combination of the coding characteristic and the analyte-interaction sites and/or corresponding analyte-bearing sites on the particles in each category being different from the combination of the coding characteristic and the analyte-interaction sites and/or corresponding analyte-bearing sites on the particles in other categories;

the method comprising examining, one at a time, each particle of a representative sample of the particles, the examination comprising:

(A) determining the coding characteristic of the particle, including whether the particle is a single-assay particle or a dual-assay particle;

(B) subjecting the particle to radiation from a laser which causes fluorescence of any fluorochromic signal dye associated with analyte-bearing sites on the particle;

(C) assessing the fluorescence caused by the laser and falling within a first wavelength band;

(D) assessing the fluorescence caused by the laser and falling within a second wavelength band; and (E) when the fluorescence assessed in steps (C) and (D) results from only a single signal dye, combining the fluorescence in the first wavelength band and the fluorescence in the second wavelength band, and when the fluorescence assessed in steps (C) and (D) results from two or more signal dyes, recording separately the fluorescence in the first wavelength band and the fluorescence in the second wavelength band.

9. A method according to claim 8 wherein (A) the plurality of particles includes (i) dual-assay particles containing analyte-bearing sites which (a) have interacted with a first analyte and have associated therewith a first fluorochromic signal dye, or (b) have interacted with a second analyte and have associated therewith a second fluorochromic signal dye; and (ii) single-assay particles containing analyte-bearing sites which have interacted with an analyte and have associated therewith a fluorochromic signal dye which is the same as the first or the second signal dye or is different therefrom;

(B) the laser (i) causes the first fluorochromic signal dye, if present, to fluoresce in a first spectrum, (ii) causes the second fluorochromic signal dye, if present, to fluoresce in a second spectrum which is different from but overlaps the first spectrum, and (iii) causes the fluorochromic signal dye or dyes associated with the single-assay particles, if present, to fluoresce in a spectrum which includes at least one of the first wavelength band and the second wavelength band.

10. A method according to claim 9 which includes assessing the fluorescence in an intermediate wavelength band between the first and second wavelength bands, and, when the fluorescence assessed in steps (C) and (D) results from only a single signal dye, combining the fluorescences in the first, second and third wavelength bands.

* * * * *